United States Patent

Bedard

[11] Patent Number: 5,312,669
[45] Date of Patent: May 17, 1994

[54] THERMOPLASTIC COMPOSITE REINFORCEMENT AND METHOD FOR ORTHOTIC, PROSTHETIC AND OTHER DEVICES

[75] Inventor: Gary Bedard, San Mateo, Calif.

[73] Assignee: Becker Orthopedic Appliance Company, Troy, Mich.

[21] Appl. No.: 818,024

[22] Filed: Jan. 3, 1992

[51] Int. Cl.⁵ ............................................. B32B 5/12
[52] U.S. Cl. ...................................... 428/105; 428/110; 428/112; 428/113; 428/114; 428/174; 428/284; 428/285; 428/220; 428/516; 428/517; 428/426; 428/474.4; 428/476.3; 623/16; 623/33; 623/34; 623/35; 623/36
[58] Field of Search ............... 428/105, 110, 113, 114, 428/112, 174, 292-295, 516, 517, 474.4, 213, 426, 476.3, 284, 285, 902, 220; 623/33-36, 16; 36/145, 154; D24/155

[56] References Cited

U.S. PATENT DOCUMENTS

| | | | |
|---|---|---|---|
| 2,917,844 | 12/1959 | Scholl | 36/71 |
| 3,644,165 | 2/1972 | Chen | 428/110 |
| 4,034,138 | 7/1977 | Babayan | 428/378 |
| 4,044,188 | 8/1977 | Segal | 428/283 |
| 4,201,612 | 5/1980 | Figge | 156/224 |
| 4,289,122 | 9/1981 | Mason et al. | 128/80 E |
| 4,425,980 | 1/1984 | Miles | 181/208 |
| 4,439,934 | 4/1984 | Brown | 36/44 |
| 4,469,543 | 9/1984 | Segal et al. | 156/283 |
| 4,532,169 | 7/1985 | Carley | 428/109 |
| 4,602,442 | 7/1986 | Revill et al. | 36/44 |
| 4,610,101 | 9/1986 | Brown | 36/44 |
| 4,688,338 | 8/1987 | Brown | 36/44 |
| 4,774,954 | 10/1988 | Ibrahim | 128/581 |
| 4,778,717 | 10/1988 | Fitchmun | 428/246 |
| 4,784,123 | 11/1988 | Robeson | 128/90 |
| 4,793,330 | 12/1988 | Honeycutt et al. | 428/254 |
| 4,888,225 | 12/1989 | Sandvig et al. | 428/71 |
| 5,112,667 | 5/1992 | Li | 428/105 |

Primary Examiner—Ellis P. Robinson
Assistant Examiner—Nasser Ahmad
Attorney, Agent, or Firm—Jenner & Block

[57] ABSTRACT

A thermoplastic composite reinforcing sheet material useful for reinforcing orthotic devices and other articles, such as a prosthetic socket or a ski boot. The composite sheet material consists of a plurality of layers. Two layers form outer opposed sides of the sheet and are made from a thermoplastic material. The core of the sheet consists of a plurality of fiber-containing layers. Each layer is impregnated with a thermoplastic resin which will bond with the outer thermoplastic layers when the final shape is vacuum thermoformed. The orientation of the fibers in the core may be varied to change the strength and rigidity of the composite thermoplastic reinforcing sheet. An orthotic device can be built using a thermoplastic host material and the disclosed thermoplastic composite reinforcing sheet material. The host material defines the overall shape of the orthotic device and is any thermoformable thermoplastic. The reinforcing sheet is used to reinforce desired sections of the final orthotic device.

31 Claims, 3 Drawing Sheets

THERMOPLASTIC COMPOSITE REINFORCEMENT AND METHOD FOR ORTHOTIC, PROSTHETIC AND OTHER DEVICES

FIELD OF THE INVENTION

This invention relates to orthotic and prosthetic devices and more particularly to materials and methods for reinforcing orthotic and prosthetic devices and the resulting devices.

BACKGROUND OF THE INVENTION

Orthotics are prescribed for a broad range of muscular or joint-related inefficiencies and ailments. An orthotic device may be custom made or made in standard sizes. The customized fit is usually achieved by using a positive mold of the portion of the body over which the orthotic device is intended to be worn. One current practice is to cast the body part with plaster of paris. Once removed from the body, the cast is called a negative model. The cast is dammed off and filled with a slurry mixture of plaster of paris and is allowed to harden. Then, the cast is removed and a plaster edition of the body part is provided called a positive model.

Three general types of materials can be used to shape the orthotic device once a positive mold of the body segment has been provided: thermoplastic resin materials, thermoplastic composite materials, and thermoset composite materials. Each type of material has its own inherent advantages and difficulties.

A primary advantage of thermoplastic resin materials is ease of construction of the orthotic or prosthetic device. These materials can be vacuum thermoformed on the positive mold to thereby provide a customized device. One current fabrication method is to use a monolithic sheet resin, such as polypropylene, heated in a convection oven and drape molded over the positive model. An internal vacuum source assures compliance of the thermoplastic to the positive model. Vacuum thermoforming provides an intimate fit and the transmission of very fine corrective forces from the orthosis to the body segment.

One drawback with thermoplastic resin materials stems from the material is flexibility which makes vacuum thermoforming possible. Thermoplastic resin materials tend to suffer from a lack of ultimate strength and rigidity. To ensure proper rigidity, orthotic devices constructed entirely from thermoplastic resin materials must be quite thick. If too thin, the device may be of limited corrective benefit. For example, when polypropylene is used in a lower extremity device such as an ankle foot orthosis (AFO), the weight of the patient may be sufficient to overcome the rigidity of the orthosis. The corrective benefit inherent in the design of the orthosis would be at least partially lost.

Unlike thermoplastic resin materials, thermoset composite materials can be very rigid and strong. In these materials, layers of fibrous materials impregnated with a thermoset adhesive are used to construct the orthotic or prosthetic device. As disclosed in U.S. Pat. No. 4,439,934, the strength and rigidity of the device can be customized by varying the types of fibers used, and by varying the nap of the fiber layers relative to the stress lines in the orthotic device.

Thermoset composite materials, however, suffer from extremely cumbersome and labor intensive fabrication techniques. Typically, each fiber layer must be individually sized and draped on the positive mold. The final composite is then cured under appropriate conditions.

Thermoset composite materials suffer from two additional difficulties. First, the fiber materials used in constructing the composites can make the final orthotic device very heavy, especially in comparison to devices made solely from thermoplastic resin materials. Second, the fiber materials used to construct the laminated composite are themselves expensive, and greatly increase the cost of the final orthotic device.

As disclosed in U.S. Pat. No. 4,778,717, some thermoplastic composite materials have been used to construct orthotic devices. In a typical construction, a core of thermoplastic material is encapsulated within layers of fiber materials impregnated with the same thermoplastic.

Orthotic devices constructed from these thermoplastic composite materials may avoid some of the problems associated with pure thermoplastics and with thermoset composites. For example, unlike thermoset composites, the thermoplastic composite can be vacuum thermoformed, thus permitting the ease of construction associated with pure thermoplastic materials. The use of external fiber layers increases the strength and rigidity of the orthotic device, thus overcoming the inherent lack of rigidity and strength associated with pure thermoplastics.

Although some of the problems associated with pure or unreinforced thermoplastics and with thermoset composites are overcome by using thermoplastic composite materials to fabricate orthotic devices, these materials nonetheless present some difficulties. The fibers used in the thermoplastic composite make the entire orthotic devices strong and rigid. Thus strength may be provided where it is not particularly needed thereby adding unnecessarily to the weight and material cost of the orthotic device.

Prosthetic devices are manufactured devices for replacing a missing body part, such as a limb or portion thereof. Prosthetic devices that are composed of endoskeletal components typically use a thermoplastic socket for the interface with the residual limb. Endoskeletal prosthetics have components between the socket and the prosthetic foot typically made of metal or plastic materials covered with a non-load bearing soft foam cover shaped to an anatomical profile. The cover is more lifelike than exoskeletal prosthetic devices. Thermoplastic sockets are susceptible to the same disadvantages as orthotic devices when the sockets are made of thermoplastic sheet material in a thermo vacuum-forming process or of other materials as previously described.

An improved material and method is needed to overcome the problems associated with the materials currently used in fabricating orthotic and prosthetic devices. Specifically, it would be advantageous to provide a material and method which can provide an orthotic device that has sufficient strength and rigidity in needed areas without unnecessarily adding to the weight and material cost of the orthotic device.

SUMMARY OF THE INVENTION

In accordance with the present invention, a thermoplastic composite reinforcing sheet material is provided that is useful in reinforcing orthotic and prosthetic socket devices. The invention is useful for both custom fit and off the shelf devices. The thermoplastic composite reinforcing sheet material is composed of two general types of materials: thermoplastic film and oriented fiber materials. The core of the thermoplastic composite reinforcing sheet consists of a plurality of thermoplastic impregnated oriented fiber layers. At least one or both outer surfaces are constructed of thermoplastic film devoid of any fibers. The core of oriented fiber materials is impregnated with a thermoplastic which will bond with the outer thermoplastic layers. The outer thermoplastic layers in turn consist of a thermoplastic which will bond, such as during vacuum thermoforming of the orthotic device with a host thermoplastic material to form a resulting orthotic device and thus provide reinforcement and strength in desired areas of the orthotic device.

The thermoplastic impregnated fiber materials used in the core of the thermoplastic composite reinforcing sheet can be oriented to alter and customize the strength and rigidity of the reinforcement. The strength and rigidity of the thermoplastic composite reinforcing sheet can be further altered by using more than one type of fiber in the core.

Also in accordance with the present invention, a device, such as an orthosis or prosthetic socket, reinforced with the thermoplastic composite reinforcing sheet material is provided. A host layer of thermoplastic host material (typically monolithic material) defines the overall shape of the orthotic device or prosthetic socket. Desired areas of the device are reinforced, preferably during fabrication of the device, with a desired shape of the thermoplastic composite reinforcing sheet material. The outer surfaces of the reinforcing sheet material consist of a thermoplastic with which the host thermoplastic material is bonding compatible. At least one of these outer thermoplastic surfaces is devoid of fibers thus ensuring that the contact surface between the device and the user is smooth so that the user does not feel the presence of the fibers. While not preferred, the reinforcing material can be utilized without one or both of the outer layers of thermoplastic.

The thermoplastic impregnated core of oriented fibers, in the composite reinforcing sheet material, provides strength and rigidity in the areas of the orthotic device reinforced with the composite. The direction of orientation of these fibers can be altered to customize the amount of strength and rigidity, and to provide specific axes of strength and rigidity.

Because the final device is not constructed entirely from the thermoplastic composite material but is only reinforced with the composite material in desired areas, the total weight gain due to the fiber content is minimized. Moreover, the use of the composite material to reinforce sections of the final orthotic device or prosthetic socket ensures that the expensive fiber materials are not wasted in non-critical areas thus minimizing the expense of using these fiber materials.

In accordance with the invention, a method for making a reinforced orthotic device and prosthetic socket is also provided. According to this method, a sheet of thermoplastic composite reinforcing material of a desired size for reinforcing a desired area of the device is provided. This sheet material is shaped to conform to the desired shape of the reinforced area. A sheet or layer of thermoplastic host material which is bonding compatible with the outer layers of the thermoplastic reinforcing composite sheet is also provided. The thermoplastic host material is then shaped to conform to the desired shape of the device. The properly sized and shaped thermoplastic composite reinforcing sheet is bonded to the desired area of reinforcement, preferably on the interior of the thermoplastic host material. Preferably, the bonding of the host and reinforcing sheet occurs during shaping of the thermoplastic host.

DESCRIPTION OF THE PREFERRED EMBODIMENT OF THE INVENTION

Figures 1, 2, 3:
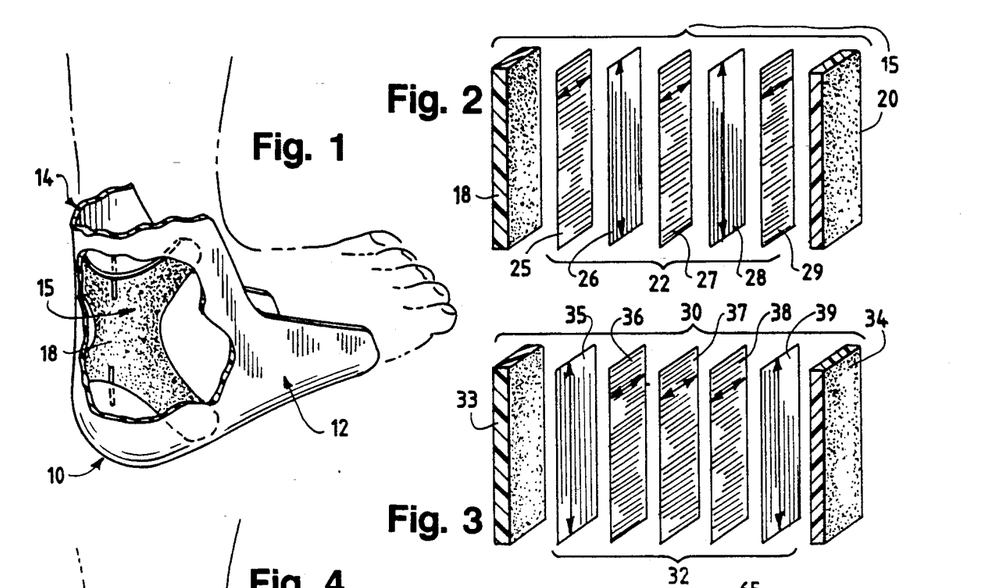
FIG. 1 is a rear perspective view of an ankle-foot orthosis with cutaway sections showing the thermoplastic composite reinforcing sheet material.
FIG. 2 is an exploded view of a thermoplastic composite reinforcing sheet material of the invention illustrating the individual layers therein.
FIG. 3 is an exploded view of another thermoplastic composite reinforcing sheet material of the invention illustrating the layers therein with the fibers in the core aligned in varying orientations.

FIG. 1 illustrates a completed reinforced ankle-foot orthosis 10. Ankle-foot orthosis 10 has been reinforced with a thermoplastic composite reinforcing sheet material 15. Ankle-foot orthosis 10 consists of a monolithic thermoplastic host material 12 shaped to conform to the desired shape of the finished orthosis, and thermoplastic composite reinforcing sheet material 15. In this embodiment, host material 12 is shaped to provide support for the ankle and foot of the user.

Host material 12 can be any thermoformable plastic such as polypropylene, polyethylene, or "TPE" having suitable characteristics for an orthosis, in this case an ankle-foot orthosis. Host material 12 in this case is polypropylene which typically has a thickness of about 0.188 (3/16) inches. Although thermoplastic composite reinforcing sheet material 15 consists of a plurality of layers, including an outer layer 18 adjacent to host material 12 as shown in FIG. 1. Thermoplastic composite reinforcing sheet material 15 has a second outer layer 20 (illustrated in FIG. 2) which forms an opposed side to outer layer 18. Outer layer 18 and opposed outer layer 20 are composed of any thermoplastic material which is bonding compatible with host material 12, in this case layers 18 and 20 being polypropylene. For example, outer layer 18 and opposed outer layer 20 are bonding compatible with host material 12 if the two materials bond together when the device is vacuum thermoformed. For example, two outer layers 18 and 20 and host material 12 would be bonding compatible if host material 12 and outer layers 18 and 20 are polypropylene. Similarly, the materials are bonding compatible if host material 12, outer layer 18 and the opposed outer layer 20 are polyethylene, or if host material 12 is TPE, and outer layers 18 and 20 are polypropylene.

Thermoplastic composite reinforcing sheet material 15 has been sized, shaped and positioned on ankle-foot orthosis 10 to provide support in the area of the Achilles tendon. Thermoplastic composite reinforcing sheet material 15 is also positioned away from the top end 14 (shown cut away in FIG. 1) of orthosis 10 to ensure that the fiber core of reinforcing sheet material 15 is not exposed and therefore that the user will not feel the fibers in the core.

FIG. 2 is an exploded view of thermoplastic composite reinforcing sheet material 15 prior to being cut to a desired shape as illustrated in FIG. 1. Thermoplastic composite reinforcing sheet material 15 consists of a plurality of layers, including a core of a plurality of bonded internal layers of oriented fibers 22 and two outer layers 18 and 20. In this embodiment, sheet material 15 is about 0.078 inches thick. Outer layers 18 and 20 are polypropylene. Typically, each layer 18 and 20 is about 0.005 inches thick. At least one of outer layers 18 and 20 should be devoid or essentially devoid of any fibers to ensure that the surface of the layer adjacent to the user is smooth and that the user does not feel any of the fibers in thermoplastic composite reinforcing sheet material 15. Thus if outer layer 18 is adjacent the host material in an orthotic device and outer layer 20 is adjacent to the user, outer layer 20 should be devoid of fibers. Preferably, both layers 18 and 20 are initially devoid of fibers, although a minor amount of fiber may migrate from core 22 into layers 18 and 20 during fabrication. As used herein, "devoid" of fibers does not exclude all fibers since a minor amount of fiber can migrate into layers 18 and 20 during fabrication of material 15. It is important that no fibers can be felt on at least one surface of sheet material 15 so that the wearer of the device incorporating sheet material 15 is protected from and does not otherwise feel the fibers, since discomfort could result. Outer layer 18 or 20 also provides an extra amount of resin for bonding to the host material.

Core 22 consists of a plurality of bonded internal layers of oriented fibers 25, 26, 27, 28, and 29. Although five such internal layers are present in sheet 15, the invention is not limited to any specific number making up the plurality of fiber layers within core 22. The number of layers may be varied as desired to provide the desired strength and rigidity of core 22. Each internal layer of core 22 is impregnated with a thermoplastic resin which is bonding compatible with outer layers 18 and 20. The thermoplastic resin of core 22 and outer layers 18 and 20 are bonding compatible if they bond when the final device is vacuum thermoformed or when sheet 15 is fabricated. For example, if outer layers 18 and 20 are polypropylene, then a polypropylene thermoplastic resin will be bonding compatible. Similarly, bonding compatibility exists if outer layers 18 and 20 and the thermoplastic resin are polyethylene. Other combinations of bonding compatible thermoplastic resins are known to those skilled in the art.

In FIG. 2, internal layers 25, 26, 27, 28, and 29 are oriented such that the fibers in each internal layer are 90° to the fibers in the adjacent internal layers. Internal layers 25, 26, 27, 28, and 29 are composed of E-glass fibers. Other suitable fibers that can be used include S-glass and KEVLAR, which is an aromatic polyamide and is a trademark of E.I. Dupont Company, Wilmington, Delaware. A basis for this phrase is found in FIGGE (4,201,612) in col. 1, lines 42–43, MILES (4,425,980) in col. 5, lines 67–68.

FIG. 3 is an exploded view of a reinforcing sheet material 30, which is another embodiment of thermoplastic composite reinforcing sheet material in accordance with the invention. Thermoplastic composite reinforcing sheet material 30 consists of a plurality of layers, including a core 32 of bonded internal layers of oriented prepreg fibers 35–39 and two outer thermoplastic layers 33 and 34. Outer layers 33 and 34 are a thermoplastic film material which is bonding compatible with a desired thermoplastic host material that will be used to define the shape of a resulting orthotic device. At least one of the outer layers 33 and 34 should be devoid of any fibers to ensure that the layer adjacent to the user is smooth and that the user does not feel any of the fibers in thermoplastic composite reinforcing sheet material 30.

The number of layers of core 32 may be as desired to provide the desired strength and rigidity characteristics of sheet 30. Each internal layer 35–39 of core 32 is impregnated with a thermoplastic resin which is bonding compatible with outer layers 33 and 34. Typically, the internal prepreg layers have a composition by weight of about 60% fiber and about 40% resin. The composite reinforcing sheet material can be made by bringing the various layers together in the desired orientation and then applying sufficient heat and pressure to bond them together. Such methods of bonding together prepreg fibers are well known in the art and therefore are not described in detail here.

Thermoplastic composite reinforcing sheet material 30 differs from sheet material 15 of FIG. 2 in the orientation of the fibers in the internal layers of core 32. The two outermost internal layers 35 and 39 are oriented such that the fibers in 35 are parallel those in 39. The three innermost layers 36, 37, and 38 are oriented such that the fibers in 37 are parallel to those in adjacent layers 36 and 38, and are 90° to the fibers in outermost internal layers 35 and 39. The overall orientation provides a strength and rigidity bias in thermoplastic composite reinforcing sheet 30.

Internal layers 35, 36, 37, 38, and 39 can be fibers selected from the group of E-glass, S-glass and KEVLAR. Alternatively, more than one type of fiber material may be used to make the internal layers. For example, innermost layer 37 may consist of carbon fibers such as graphite and the remaining layers may be selected from the group consisting of E-glass, S-glass, and KEVLAR. Changing the type of fiber used in the innermost layer can affect the strength and rigidity bias established by the overall orientation of the internal fibers.

The orientation of the fiber layers in the core of the reinforcing sheet is not limited to those orientations depicted in FIG. 2 and FIG. 3. For example, any desired orientation can be utilized, including orientations in which the fibers of one layer are parallel or non-parallel to the fibers of adjacent layers. Woven fibers impregnated with thermoplastic resin could also be used for one or more of the internal layers of the core. As a further example of a reinforcing sheet configuration, the sheet could be composed of four core layers of prepreg fiber having a 0°-90°-0°-90°. layer to layer fiber orientation. The prepreg layers may be of different fibers. For example, in the foregoing example, the two inner fiber layers can be carbon and the two outer layers can be E-glass. Another example of a reinforcing sheet configuration has six core layers of fiber having a layer orientation of 0°-45°-90°-45°-90°-0°.

Figures 4, 5, 6:
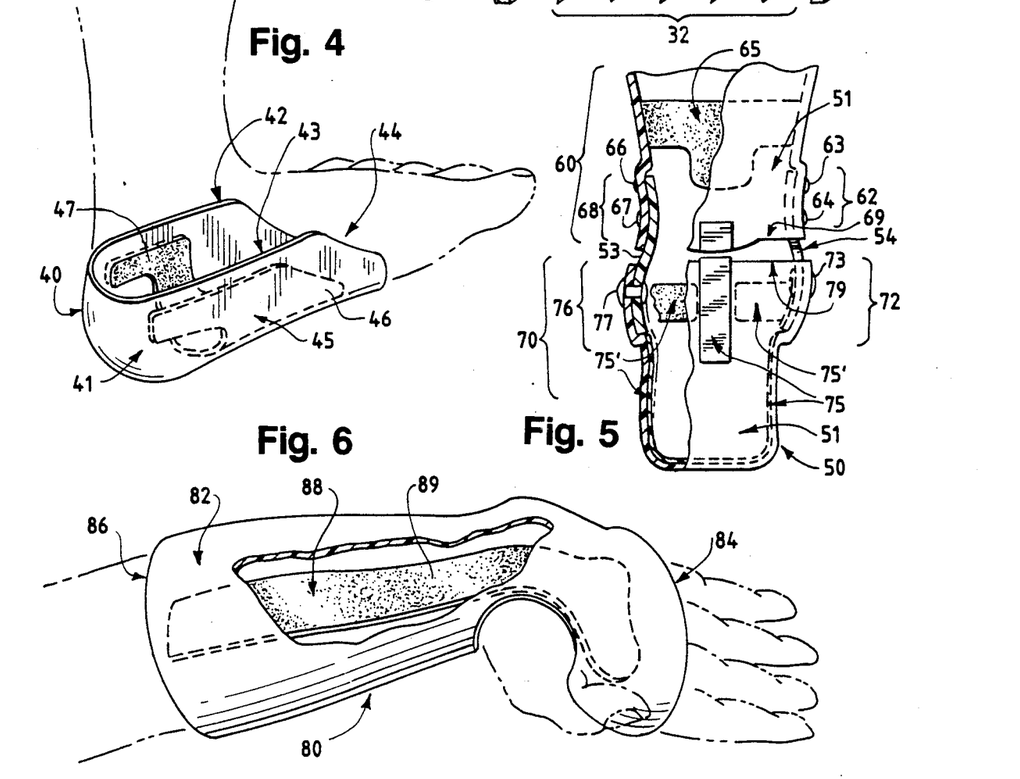
FIG. 4 is a rear perspective view of a foot orthosis in which the placement of the thermoplastic composite reinforcing sheet material is shown in phantom.
FIG. 5 is a rear elevation view of an articulated ankle-foot orthosis with cutaway sections showing the thermoplastic composite reinforcing sheet material.
FIG. 6 is a perspective fragmentary view of a wrist orthosis showing the thermoplastic composite reinforcing sheet material.

FIG. 4 is a rear perspective view of a foot orthosis 40 in which the placement of the thermoplastic composite reinforcing sheet material 45 is defined by a phantom line. Foot orthosis 40 consists of a host material 41 and a thermoplastic composite reinforcing sheet material 45. Host material 41 defines the overall shape of foot orthosis 40 and is any thermoformable plastic. Thermoplastic composite reinforcing sheet material 45 can be similar to sheet material 15 or 30 and is sized, shaped and positioned to support the calcaneal area of the user's foot. Composite reinforcing sheet material 45 is also positioned away from trimlines 42, 43, and 44 to ensure that the user does not feel the fibers in composite reinforcing sheet material 45.

Two outer and opposed layers 46 and 47 of composite reinforcing sheet material 45 are shown in FIG. 4. As with reinforcing sheets 15 and 30, outer layers 46 and 47 are any thermoplastic which is bonding compatible with host material 41. Outer layer 46 is adjacent host material 41. Outer layer 47 is adjacent the user and therefore should be devoid of fibers to ensure that the user does not feel any fibers.

FIG. 5 is a rear elevation view, partially cut away, of a portion of an articulated ankle-foot orthosis 50 with cutaway sections showing the thermoplastic composite reinforcing sheet material. Ankle-foot orthosis 50 has two portions, a calf portion 60 and a foot portion 70. Calf portion 60 and foot portion 70 are similar to calf portion 140 and foot portion 160 of knee-ankle-foot orthosis 100 hereafter described. Thermoplastic host material 51 is present in both portions and defines the final overall shape of calf portion 60 and foot portion 70.

Calf portion 60 contains an area reinforced by thermoplastic composite reinforcing sheet material 65. Composite reinforcing sheet material 65 is sized, shaped and positioned to provide support for the upper portion of the Achilles tendon and is positioned away from trimline 69 of calf portion 60. Composite reinforcing sheet material 65 consists of a plurality of layers (not shown) and can be similar to sheets 15 or 30. Two outer layers which form opposed sides are any thermoplastic which is bonding compatible with host material 51.

Calf portion 60 has two raised sections 62 and 68 which accommodate the separate joint sections 53 and 54 which join together calf portion 60 and foot portion 70. Joint sections 53 and 54 are thermoplastic suitable for thermo vacuum-forming. Rivets 63, 64, 66, and 67 attach joint sections 53 and 54 to calf portion 60.

Foot portion 70 and calf portion 60 includes a thickened thermoplastic area or block 75 located on outer portions thereof, reinforced by a thermoplastic composite reinforcing sheet material 75'. Composite reinforcing sheet material 75' is positioned in orthosis 50, so that when worn, area 75 is located adjacent the back middle portion of the user's ankle and extends above foot portion trimline 79. Area 75 functions as a stop to limit the flexing of the user's ankle and is reinforced by reinforcing sheet material 75'. Reinforcing sheet material 75' extends from each side of the calcaneal saddle of reinforcing material, such as illustrated in FIG. 4, and extends to the sides of block 75.

Composite reinforcing sheet material 75' can be obtained from sheet 15 or 30, for example.

Foot portion 70 has two raised sections 72 and 76 which accommodate separate joint sections 53 and 54. Coat screws 73 and 77 attach joint portions 53 and 54 to foot section 70 and permit pivoting of joint sections 53 and 54 about screws 73 and 77.

FIG. 6 is a perspective view of a wrist orthosis 80 with cutaway sections showing thermoplastic composite reinforcing sheet material 88. Wrist orthosis 80 consists of a thermoplastic host material 82 and thermoplastic composite reinforcing sheet material 88. Host material 82 is a thermoformable plastic and defines the overall shape of the orthosis. Composite reinforcing sheet material 88 is similar to sheet 15 or 30. In this embodiment, composite reinforcing sheet material 88 is sized, shaped, and positioned to provide support for the palmar muscle region of the ventral side of the user's forearm, wrist, and palm. Composite reinforcing sheet material 88 is positioned away from trimlines 84 and 86 of orthosis 80.

An outer layer 89 of sheet 88 is illustrated in FIG. 6 adjacent host material 82.

Figures 7, 8, 9:
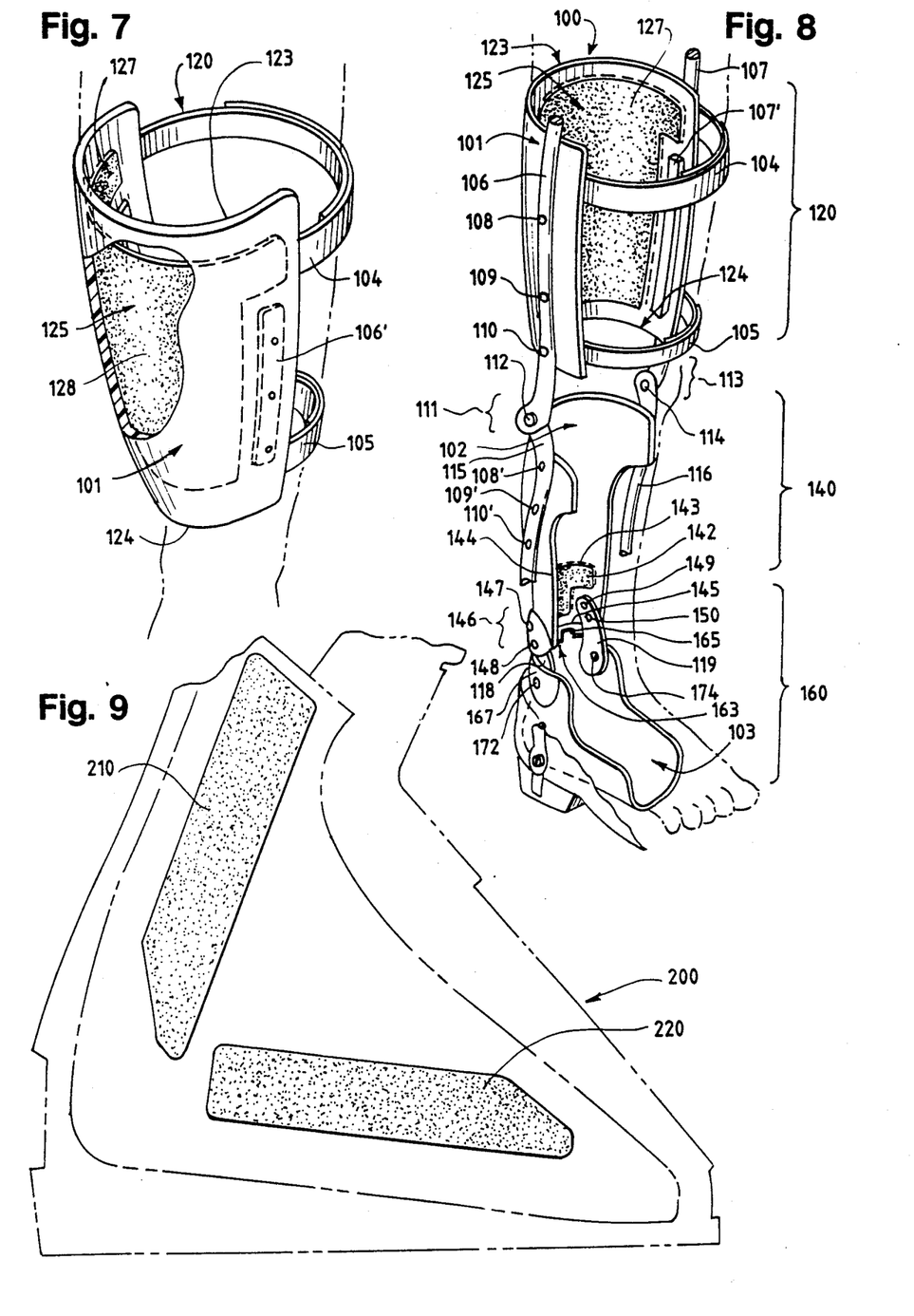
FIG. 7 is a rear perspective fragmentary view of an upper thigh orthosis showing the thermoplastic composite reinforcing sheet material.
FIG. 8 is a front perspective view of an articulated knee-ankle-foot orthosis.
FIG. 9 is a side elevation view of a ski boot showing sections reinforced with the thermoplastic composite reinforcing sheet material in accordance with the invention.

FIG. 8 is a front perspective of an articulated knee-ankle-foot orthosis 100. Knee-ankle-foot orthosis 100 has three portions: an upper thigh portion 120, a calf portion 140, and a foot portion 160. The final shape of upper thigh portion 120, calf portion 140, and foot portion 160 are defined by the host materials 101, 102, and 103 respectively, which are thermoplastic material that is suitable for thermo vacuum-forming.

Upper thigh portion 120 illustrated in FIGS. 7 and 8, includes thermoplastic host material 101 and a composite reinforcing sheet material 125. Composite reinforcing sheet material 125 is formed from sheet 15 or 30, for example, and is sized, shaped, and positioned to provide support for the user's posterior femoral muscles. Composite reinforcing sheet material 125 is positioned away from the trimlines 123 and 124. Host material 101 defines the final overall shape of upper thigh portion 120. Upper thigh portion 120 is secured to the user's thigh by Velcro straps 104 and 105.

Of the plurality of layers which form composite reinforcing sheet 125, outer layer 127 adjacent to the user is shown in FIGS. 7 and 8 and outer layer 128 is shown in FIG. 7. Outer layer 127 should be devoid of any fibers. Second outer layer 128 forms an opposed side to outer layer 127. Outer layers 127 and 128 are made from any thermoplastic which is bonding compatible with host material 101.

Two sidebars 106 and 107 are attached to the lateral reinforced portions 106' and 107' of upper thigh portion 120 by rivets, namely, rivets 108, 109, and 110 for sidebar 106 (the rivets for sidebar 107 not shown). Lateral reinforced portions 106' and 107' can be formed from appropriately sized pieces of sheet 15 or 30, for example, bonded to host material 101. Sidebars 106 and 107 terminate in two joints 111 and 113 below upper thigh portion 120. Screws 112 and 114 attach sidebars 106 and 107 to lower sidebars 115 and 116 and permit movement at joints 111 and 113.

Velcro straps can be provided to secure calf portion 140 to the user

Lower sidebars 115 and 116 extend to calf portion 140 and are attached thereto by rivets 108', 109' and 110' for lower sidebar 115 (the rivets for sidebar 116 not shown). Host material 102 defines the overall shape of calf portion 140. Calf portion 140 contains an area reinforced by thermoplastic composite reinforcing sheet material 142. Reinforcing sheet material 142 is obtained from sheet 15 or 30, for example, and is sized, shaped, and positioned to provide support for the upper portion of the Achilles tendon area. Reinforcing sheet material is also positioned away from trimlines 144 and 145 of calf portion 140.

Composite reinforcing sheet material 142 consists of a plurality of layers (not shown). Two outer layers, outer layer 143 and a second outer layer (not shown) which forms an opposed side to outer layer 143, can be any thermoplastic which is bonding compatible with host material 102. Outer layer 143 which is adjacent to the user should be devoid of any surface fibers.

Calf portion 140 has two raised sections, section 146 and a second opposed raised section (not shown) which accommodate the separate joint sections 118 and 119 joining calf portion 140 and foot portion 160. Joint sections 118 and 119 are thermoformable plastic. Rivets 147 and 148, and rivets 149 and 150 attach joint sections 118 and 119 respectively to calf portion 140.

Host material 103 is a thermoformable plastic which defines the overall shape of foot portion 160. Foot portion 160, similar to foot orthosis 40, also contains a raised portion of thermoplastic material 165. Thermoplastic material 165 is positioned in the back middle portion of the user's ankle and terminates below foot portion trimline 163 and acts as a stop as previously described with respect to FIG. 5.

Composite reinforcing sheet material 142, which can be obtained from sheet 15 or 30, for example, consists of a plurality of layers (not shown). Two outer layers which form opposed sides, outer layer 143 and the second opposed layer (not shown) are any thermoplastic which is bonding compatible with host material 102. Outer layer 143 is adjacent the user and should therefore be devoid of any fibers.

Foot portion 160, similar in shape and reinforced as foot orthosis 40, has two raised sections 167 and a second opposed raised section (not shown) which accommodate separate joint sections 118 and 119. Coat screws 172 and 174 attach joint portions 118 and 119 to foot section 160 and permit pivoting of joint sections 118 and 119 about screws 172 and 174.

FIG. 9 illustrates a side elevation view of an article to be worn by a person, which in this case is a boot, namely, a ski boot 200. Two areas of ski boot 200 are reinforced with composite reinforcement sheets 210 and 220. Composite reinforcements sheets 210 and 220 are obtained from, for example, sheet 15 or 30, and consist of a plurality of layers (not shown). Ski boot 200 is at least partly constructed of thermoplastic material or other material which forms the overall shape of the boot and incorporates sheets 210 and 220 therein in areas where reinforcement of boot 200 is desired. Generally, at least these areas of boot 200 adjacent the reinforcement sheets 210 and 220 are made of a bonding compatible thermoplastic.

Figures 10, 11:
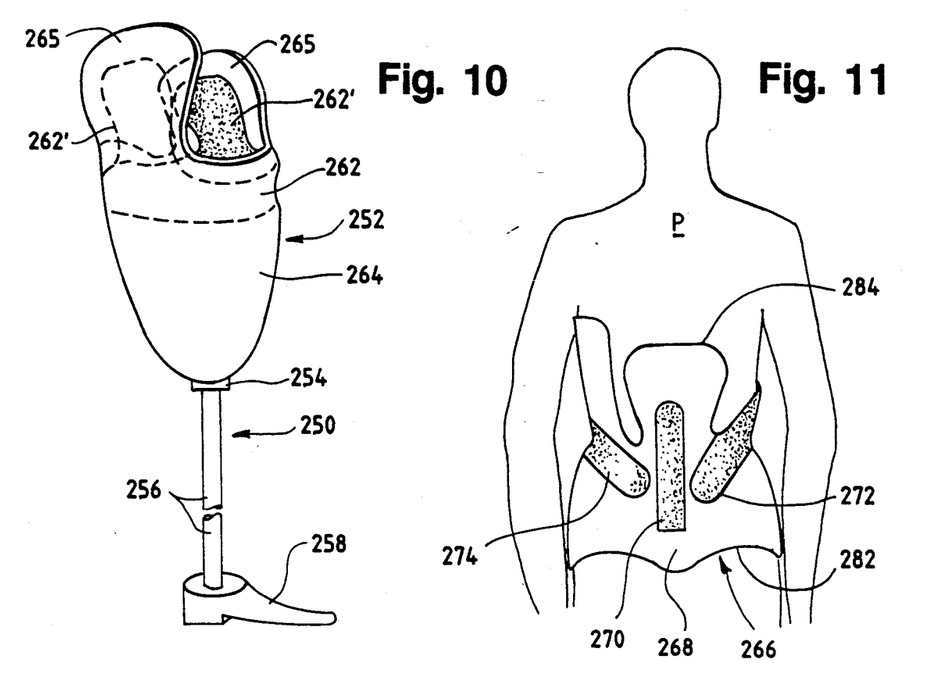
FIG. 10 is a perspective view of a below knee endoskeletal prosthesis.
FIG. 11 is a front elevation view of a spinal orthosis in accordance with the invention.

FIG. 10 illustrates a prosthetic leg 250 of the type worn by a below-the-knee amputee. Leg 250 includes a generally rigid thermoplastic socket 252 fixed to an upper end 254 of a vertical brace 256. An artificial foot 258 is attached to the lower end of brace 256. Brace 256, foot 258 and socket 252 are well known devices in the art. For example, see U.S. Pat. No. 4,923,475. The shape of the inside surface of rigid socket 252 is usually molded to fit the general anatomical configuration of the limb to be supported. The size of rigid socket 252 should be slightly greater than the limb to provide clearance for a sock (not shown).

Rigid thermoplastic socket 252 includes a reinforced area 262. Reinforced areas 262 and 262' are composed of reinforced thermoplastic composite sheet material in accordance with the invention, such as material 15 or 30, for example, which has been bonded to host material 264 of socket 252 such as by thermo- vacuum-forming, for example. Area 262 is a band that wraps around the brim of socket 252. Ears 265 of socket 252 are reinforced by areas 262' and thus give a more stable socket giving the patient an increase in stability.

Figure 12:
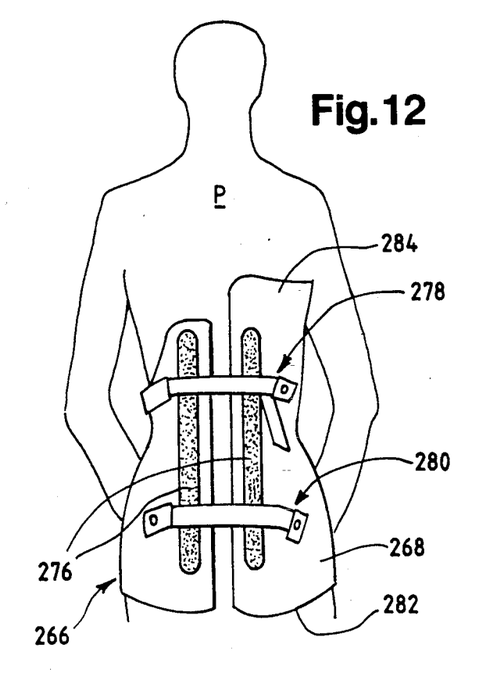
FIG. 12 is a rear elevation view of the spinal orthosis of FIG. 11.

Referring to FIGS. 11 and 12, there is illustrated a spinal orthosis, specifically a thorocolumbarsacral orthosis (TLSO) 266 being worn by a patient P. TLSO 266 is composed of a monolithic thermoplastic body or host 268 having specific areas 270, 272, 274 and 276 reinforced by thermoplastic composite reinforcing sheet material bonded thereto. The reinforcing sheet material is in accordance with the invention, such as sheet material 15 or 30, for example, and can be located exteriorly or interiorly of host 268. Suitable strap and buckle assemblies 278 and 280 are provided in the rear of TLSO 266 for attaching TLSO 266 to patient P as shown in FIG. 12. The exact configuration of trimlines 282 and 284 is dictated by the clinical presentation.

Each of the foregoing devices can be made by the same or similar general method. The first step is to construct a positive mold of the portion of the body over which the device is intended to be worn. Next, the final size and shape of the composite reinforcing sheet material is determined. For example, if constructing an ankle-foot orthosis, the composite reinforcing sheet material may be sized and shaped to provide support for the Achilles tendon. The positive mold is used to help develop a pattern for the desired size and shape of the composite reinforcing sheet. One method for constructing a pattern for the composite reinforcing sheet involves drawing the proposed size, shape and placement of the composite reinforcing sheet directly on the positive mold with an indelible pencil. A piece of thermoplastic foam such as petite or aliplast is then placed on the desired portion of the positive mold and heat molded to the section of the model with the pencil pattern.

When the foam is removed, the indelible pencil pattern should transfer to the inner surface of the thermoplastic foam. The foam pattern is trimmed and its placement is verified on the positive model.

The foam pattern is then used to construct the desired size and shape of the composite reinforcing layer. The foam pattern should be placed on the composite thermoplastic sheet such that the placement exploits the direction of strength and rigidity in the composite reinforcing sheet. The foam pattern is traced onto the composite sheet to determine the final form of the composite sheet.

After the final form of the composite sheet has been constructed, both the final composite sheet form and the host material are heated until they are soft and pliable. The final composite sheet form is placed on the desired portion of the positive mold. The host sheet material, in a size sufficient to completely encapsulate the positive model, is immediately thereafter draped over the composite sheet and sealed around the positive model. The seal is consolidated and the internal vacuum source is activated. The combination of heat and vacuum bonds the two sheets together on the positive model.

While the invention has been described with respect to certain preferred embodiments, it is to be understood that the invention is capable of numerous changes, modifications and rearrangements that are intended to be covered by the following claims. For example, the orthotic device and method in accordance with the invention can utilize reinforcing material similar to material 15 or 30, for example, but without outer thermoplastic layers 18 and 20 or 33 and 34, respectively.

What is claimed is:

1. A reinforced orthotic or prosthetic device comprising:
   a. a layer of bonding compatible thermoplastic host material defining a desired shape of said device;
   b. a thermoplastic composite reinforcing sheet material of a desired shape bonded to the host material in a desired area comprising a plurality of thin layers bonded to one another to form a substantially unitary sheet, the layers including two outer thermoplastic layers, at least one of the thermoplastic layers being devoid of fibers so that no fibers can be felt on the surface of said layers, forming opposed sides of the composite reinforcing sheet material for bonding one or more sides of the composite reinforcing sheet material to the bonding compatible thermoplastic host material for reinforcing the thermoplastic host material, the sheet material including a core composed of a plurality of bonded internal layers of oriented fibers impregnated with a thermoplastic resin bonding compatible with the thermoplastic used in the two outer thermoplastic layers of the composite reinforcing sheet material, the impregnated thermoplastic resin being bonded to the thermoplastic used in the two outer thermoplastic layers.

2. The device of claim 1 wherein alternating layers of the core of bonded internal layers of oriented fibers of the thermoplastic composite reinforcing sheet material are oriented such that the fibers in any one of said layers are non-parallel to the fibers in adjacent bonded internal layers of oriented fibers.

3. The device of claim 2 wherein the layer of bonding compatible thermoplastic host material is polypropylene, the two outer thermoplastic layers of the thermoplastic composite reinforcing sheet material are polypropylene film and the thermoplastic bonding resin in the core of bonded internal layers of oriented fibers is polypropylene.

4. The device of claim 2 wherein the core of bonded internal layers of oriented fibers of the composite thermoplastic reinforcing sheet material is selected from the group consisting and E-Glass, S-glass or KEVLAR.

5. The device of claim 1 wherein the layer of bonding compatible thermoplastic host material is polyethylene, the two outer thermoplastic layers of the thermoplastic composite reinforcing sheet material are polyethylene film and the thermoplastic bonding resin in the core of bonded internal layers of oriented fibers is polyethylene.

6. The device of claim 1 wherein the core of bonded internal layers of oriented fibers of the composite thermoplastic reinforcing sheet material is selected from the group consisting of E-Glass, S-glass and KEVLAR.

7. The device of claim 1 wherein the layer of bonding compatible thermoplastic host material is polyethylene, the two outer thermoplastic layers of the thermoplastic composite reinforcing sheet material are polypropylene film and the thermoplastic bonding resin in the core of bonded internal layers of oriented fibers is polypropylene.

8. The device of claim 1 wherein the fibers of the bonded internal layer of oriented fibers adjacent one outer thermoplastic layer are oriented parallel to the fibers of the bonded internal layer of oriented fibers adjacent the second outer thermoplastic layer.

9. The device of claim 1 wherein the fibers of the middle bonded internal layer of oriented fibers are oriented parallel to the fibers of the adjacent bonded internal layers of oriented fibers and are oriented 90 degrees to the fibers of the bonded internal layers of oriented fibers adjacent to the two outer thermoplastic layers.

10. The device of claim 1 wherein the bonding compatible thermoplastic host material is polypropylene, the two outer thermoplastic layers of the thermoplastic composite reinforcing sheet material are polypropylene film and the thermoplastic bonding resin in the bonded internal layers of oriented fibers of the core of the thermoplastic composite reinforcing sheet material is polypropylene.

11. The device of claim 1 wherein the middle bonded internal layer of oriented fiber of said thermoplastic composite sheet material is graphite and the remaining bonded internal layers of oriented fibers are selected from the group consisting of E-glass, S-glass and KEVLAR.

12. The device of claim 1 wherein the bonding compatible thermoplastic host material defines an ankle-foot orthosis.

13. The device of claim 1 wherein the thermoplastic composite reinforcing sheet material is sized, shaped and positioned to support the area of the Achilles tendon.

14. The device of claim 1 wherein the host material defines a foot orthosis.

15. The device of claim 1 wherein the thermoplastic composite reinforcing sheet material is sized, shaped and positioned to support the calcaneal saddle for control of the sustentaculum tail.

16. The device of claim 1 wherein the host material defines an articulated ankle-foot orthosis.

17. The device of claim 1 wherein the thermoplastic composite reinforcing sheet material is sized, shaped and positioned to support the Achilles tendon.

18. The device of claim 1 wherein the host material defines a wrist orthosis.

19. The device of claim 1 wherein the thermoplastic composite reinforcing sheet material is sized, shaped and positioned to support the palmar muscle region of the ventral side of the forearm, wrist, and palm.

20. The device of claim 1 wherein the thermoplastic composite reinforcing sheet material is sized, shaped and positioned to support the posterior femoral muscles.

21. The device of claim 1 wherein the host material defines an articulated knee-ankle-foot orthosis comprising a thigh portion, a calf portion and a foot portion.

22. The device of claim 21 wherein the thigh portion includes thermoplastic composite reinforcing sheet material sized, shaped and positioned to support the posterior femoral muscles.

23. The device of claim 22 wherein the calf portion includes thermoplastic composite reinforcing sheet material sized, shaped and positioned to support the upper portion of the Achilles tendon area.

24. The device of claim 23 wherein the foot portion includes thermoplastic composite reinforcing sheet material sized, shaped and positioned to support the lower portion of the Achilles tendon area.

25. The device of claim 1 wherein the host material defines a thorocolumbarsacral orthosis.

26. The device of claim 1 wherein the host material defines a prosthetic socket.

27. The device of claim 26 wherein the reinforcing sheet material extends around the brim of the socket.

28. The device of claim 26 wherein the reinforcing material is located in the ears of the socket.

29. A reinforced orthotic or prosthetic device comprising:
a layer of bonding compatible thermoplastic host material defining a desired shape of the device;
a thermoplastic composite reinforcing sheet material of a desired shape bonded to the host material in a desired area comprising a plurality of thin layers bonded to one another to form a substantially unitary sheet, the layers including a plurality of bonded layers of oriented fibers impregnated with a thermoplastic resin bonding compatible with the thermoplastic of the host material, one side of the sheet material being bonded to the thermoplastic host material.

30. An article to be worn on the foot comprising:
a layer of bonding compatible thermoplastic host material defining a desired shape of said article;
a thermoplastic composite reinforcing sheet material of a desired shape bonded to the host material in a desired area comprising a plurality of thin layers bonded to one another to form a substantially unitary sheet, the layers including two outer thermoplastic layers, at least one of the thermoplastic layers being devoid of fibers so that no fibers can be felt on the surface of said layers, forming opposed sides of the composite reinforcing sheet material for bonding one or more sides of the composite reinforcing sheet material to the bonding compatible thermoplastic host material for reinforcing the thermoplastic host material, the sheet material including a core composed of a plurality of bonded internal layers of oriented fibers impregnated with a thermoplastic resin bonding compatible with the thermoplastic used in the two outer thermoplastic layers of the composite reinforcing sheet material, the impregnated thermoplastic resin being bonded to the thermoplastic used in the two outer thermoplastic layers.

31. A reinforced orthotic or prosthetic device comprising:
a layer of bonding compatible thermoplastic host material defining a desired shape of the article;
a thermoplastic composite reinforcing sheet material of a desired shape bonded to the host material in a desired area comprising a plurality of thin layers bonded to one another to form a substantially unitary sheet that is about 0.078 inches thick, the layers including two outer thermoplastic layers, at least one of the thermoplastic layers being devoid of fibers so that no fibers can be felt on the surface of said layers, forming opposed sides of the composite reinforcing sheet material to the bonding compatible thermoplastic host material for reinforcing the thermoplastic host material, the sheet material including a core composed of a plurality of bonded internal layers of oriented fibers impregnated with a thermoplastic resin bonding compatible with the thermoplastic used in the two outer thermoplastic layers of the composite reinforcing sheet material, the impregnated thermoplastic resin being bonded to the thermoplastic used in the two outer thermoplastic layers; wherein said outer layers are each about 0.005 inches thick.

* * * * *